United States Patent
Schjødt et al.

(10) Patent No.: US 9,273,020 B2
(45) Date of Patent: Mar. 1, 2016

(54) PROCESS FOR THE PRODUCTION OF CHEMICAL COMPOUNDS FROM CARBON DIOXIDE

(71) Applicant: Haldor Topsøe A/S, Kgs. Lyngby (DK)

(72) Inventors: Niels Christian Schjødt, Brønshøj (DK); John Bøgild Hansen, Copenhagen (DK); Claus Friis Pedersen, Vanløse (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/394,508

(22) PCT Filed: Apr. 11, 2013

(86) PCT No.: PCT/EP2013/057567
§ 371 (c)(1),
(2) Date: Oct. 15, 2014

(87) PCT Pub. No.: WO2013/164172
PCT Pub. Date: Nov. 7, 2013

(65) Prior Publication Data
US 2015/0057458 A1    Feb. 26, 2015

(30) Foreign Application Priority Data

May 2, 2012 (DK) ................................ 2012 70225

(51) Int. Cl.
| | | |
|---|---|---|
| *C07D 305/00* | (2006.01) | |
| *C07C 69/96* | (2006.01) | |
| *C07C 51/14* | (2006.01) | |
| *C07D 305/12* | (2006.01) | |
| *C07C 67/38* | (2006.01) | |
| *C07C 68/00* | (2006.01) | |
| *C07C 201/02* | (2006.01) | |
| *C07D 301/04* | (2006.01) | |
| *C25B 1/02* | (2006.01) | |
| *C25B 15/08* | (2006.01) | |
| *C25B 1/00* | (2006.01) | |
| *C07C 67/035* | (2006.01) | |
| *C07C 68/04* | (2006.01) | |

(52) U.S. Cl.
CPC .............. *C07D 305/12* (2013.01); *C07C 51/14* (2013.01); *C07C 67/035* (2013.01); *C07C 67/38* (2013.01); *C07C 68/005* (2013.01); *C07C 68/04* (2013.01); *C07C 201/02* (2013.01); *C07D 301/04* (2013.01); *C25B 1/00* (2013.01); *C25B 1/02* (2013.01); *C25B 15/08* (2013.01); *Y02E 60/366* (2013.01); *Y02P 20/133* (2015.11); *Y02P 20/134* (2015.11)

(58) Field of Classification Search
CPC ...... C07C 67/28; C07C 67/035; C07C 51/14; C07C 201/02; C07C 203/04; C07C 53/124; C07C 58/04; C07C 58/005; C07C 69/96; C07C 69/24; C07C 67/38; Y02E 60/366; C07D 305/12; C07D 301/04
USPC ............................ 549/510; 558/277; 562/521
See application file for complete search history.

(56) References Cited

U.S. PATENT DOCUMENTS

| | | | | |
|---|---|---|---|---|
| 5,705,683 | A | * | 1/1998 | Lippert et al. ................. 562/522 |
| 6,284,919 | B1 | * | 9/2001 | Pearson et al. ................ 560/233 |
| 2008/0023338 | A1 | | 1/2008 | Stoots et al. |

FOREIGN PATENT DOCUMENTS

| | | |
|---|---|---|
| CN | 1775734 A | 5/2006 |
| CN | 101747234 A | 6/2010 |
| EP | 2 816 284 A2 | 12/2014 |
| JP | 2001233796 * | 8/2001 |

OTHER PUBLICATIONS

Bidrawn et al, Efficient Reduction of CO2 in a Solid Oxide Electrolyzer, 2008, Electrochemical and Solid State Letters, 11(9) B167-B170.*

Kiyoshi Otsuka et al., "Dimethyl Carbonate Synthesis by Electrolytic Carbonylation of Methanol in the Gas Phase", Electrochimica Acta, Elsevier Science Publishers, vol. 39, No. 14, Oct. 1, 1994, pp. 2109-2115.

Meng Ni et al., Modeling of a Solid Oxide Electrolysis Cell for Carbon Dioxide Electrolysis:, Chemical Engineering Journal, Elsevier Sequoia, vol. 164, No. 1, Oct. 15, 2010, pp. 246-254.

* cited by examiner

*Primary Examiner* — T. Victor Oh
(74) *Attorney, Agent, or Firm* — Dickstein Shapiro LLP

(57) ABSTRACT

Process for the production of a chemical compound from a carbon dioxide starting material, comprising the steps of a) providing a feed stream consisting mainly of carbon dioxide; b) electrolyzing in an electrolysis stage the carbon dioxide in the feed stream to a first gas stream containing carbon monoxide and a second gas stream containing oxygen, wherein the molar ratio between carbon monoxide and oxygen is about 1:0.5 in an electrolysis stage; c) adjusting the composition of the first gas stream or the second gas stream or both gas streams to include carbon dioxide, either by operating at less than full conversion of $CO_2$ or by sweeping one or both gas streams with a gas containing $CO_2$ or by at some stage between the electrolysis cell and the oxidative carbonylation reactor diluting one or both gas streams with a gas containing $CO_2$; all while maintaining an overall molar ratio of carbon monoxide to oxygen of about 1:0.5; and d) introducing the first and second process stream into a reaction stage and reacting the first and second process stream combined or in succession with a substrate to the chemical compound by means of an oxidative carbonylation reaction with the carbon monoxide and oxygen contained in the process feed stream.

18 Claims, No Drawings

PROCESS FOR THE PRODUCTION OF CHEMICAL COMPOUNDS FROM CARBON DIOXIDE

The present invention relates to production of chemical compounds, e.g. fuels, chemicals and polymers from carbon dioxide ($CO_2$). The invention combines two known technologies, i.e. carbon dioxide electrolysis and an oxidative carbonylation reaction into an integrated process where the two technologies show mutual synergies. The invention is a process, which is environmentally benign and results in the production of valuable and much needed chemical compounds as well as in a gross consumption of carbon dioxide.

In a high-temperature electrolysis cell by the application of a current, carbon dioxide is split into carbon monoxide (CO) and oxygen ($O_2$) according to the half cell equations $$CO_2(g) + 2e^- = CO(g) + O^{2-}(\text{electrolyte}) \quad\quad 1)$$

$$O^{2-}(\text{electrolyte}) = \tfrac{1}{2}O_2(g) + 2e^- \quad\quad 2)$$

With the overall reaction being $$CO_2(g) = CO(g) + \tfrac{1}{2}O_2(g) \quad\quad 3)$$

Two separate gas streams are thus produced; namely carbon monoxide and oxygen in the molar ratio 2:1.

In the following, oxidative carbonylation reactions may be referred to as oxidative carbonylations for simplicity. Oxidative carbonylations are—usually catalytic—processes which combine carbonylation and oxidation. Normally, an "oxidative carbonylation" reaction is a term describing the simultaneous reaction of carbon monoxide and oxygen together with at least one more substrate to yield a reaction product.

The term "oxidative carbonylation" shall in context with the present invention be understood in a broader sense.

Thus, two-step reactions where at least one substrate other than CO and $O_2$ is first reacted with oxygen and the intermediate product thereof is subsequently reacted with carbon monoxide or vice versa will be considered as oxidative carbonylation processes and are considered to be part of the present invention. If the oxidative carbonylation reaction is carried out as two consecutive reactions, the individual reactions may optionally be carried out in two different reactors, optionally with different catalysts and optionally at different reaction conditions; optionally the two consecutive reactions may be carried out by introducing carbon monoxide and oxygen at different positions in the same reactor. The simultaneous reaction of carbon monoxide and oxygen together with at least one more substrate to yield a reaction product is in the following referred to as "combined oxidative carbonylation" and the above two-step processes are referred to as "successive oxidative carbonylation". These reactions may overall also be referred to as "oxidative carbonylation" and are comprised by the present invention.

In its broadest embodiment the invention relates to a process for the production of a chemical compound from a carbon dioxide comprising starting material, comprising the steps of a) providing a feed stream comprising carbon dioxide;
b) electrolysing in an electrolysis stage at least a part of the amount of the carbon dioxide in the feed stream to a first gas stream containing carbon monoxide and a second gas stream containing oxygen, wherein the molar ratio between carbon monoxide and oxygen is about 1:0.5;
c) introducing carbon dioxide into the first and/or the second gas stream either by maintaining a degree of conversion of carbon dioxide in the electrolysis stage of less than 100% and/or sweeping either the first or the second gas stream or both gas streams with a sweep gas containing carbon dioxide and/or at some stage between the electrolysis stage and a subsequent reaction stage with a gas containing carbon dioxide to obtain a first process stream containing carbon monoxide and a second process stream containing oxygen, wherein the first and/or second process stream further contains carbon dioxide and the molar ratio of carbon monoxide in the first process stream to oxygen in the second process stream is about 1:0.5; and
d) introducing the first and second process stream into the reaction stage and reacting the first and second process stream combined or in succession with a substrate to the chemical compound by means of an oxidative carbonylation reaction with the carbon monoxide and oxygen contained in the process feed stream.

It must be noted that at any degree of conversion of $CO_2$ in the electrolysis cell and no matter how the two gas streams are mixed and/or diluted the electrolysis cell will generate carbon monoxide and oxygen in a molar ratio of about 1:0.5

As already mentioned the oxidative carbonylation may also be performed in succession. Thus in an embodiment of the invention, the substrate is reacted with the first process stream prior to be reacted with the second process stream.

In further an embodiment of the invention the substrate is reacted with the second process stream prior to be reacted with the first process stream.

It is preferred that every gas stream at any position in the process has a composition which is outside the explosion regime for the given gas composition at the given temperature and pressure. This is obtained by dilution of one or both of the reactant streams with a $CO_2$-rich gas before mixing the $O_2$-containing gas stream with a reducing gas stream.

In another embodiment of the invention the oxygen containing gas is diluted with a gas rich in carbon dioxide before being cooled to the inlet temperature of the oxidative carbonylation reactor.

In yet another embodiment of the invention the oxygen containing gas is diluted sufficiently with a gas rich in carbon dioxide to ensure that the concentration by volume of $O_2$ is less than 20%; more preferably less than 10%.

In all embodiments of the invention, the electrolysis of carbon dioxide is preferably performed in a solid oxide electrolysis cell.

In all embodiments of the invention the electrolysis of carbon dioxide is preferably carried out at a pressure of between 0.1 bar and 50 bar.

Useful substrates for the oxidative carbonylation process according to the invention comprise methanol, ethylene and propene being oxidatively carbonylated to dimethyl carbonate, β-propiolactone and methacrylic acid compounds, respectively as explained in more detail by the examples which follow. Other substrates can be used for oxidative carbonylation and the above examples are not intended to limit the invention but serve merely as illustrative examples of how the invention can be applied.

The oxidative carbonylation reaction can be performed in a catalytic reactor in which both the oxygen-containing gas stream and the carbon monoxide-containing gas stream are introduced into the reactor.

Alternatively the reaction can be performed in separate steps, an oxidation reaction in a first reactor by introducing the oxygen-containing gas stream to the reactor in the presence of a substrate and carrying out the oxidation reaction at one set of reaction conditions, followed by a carbonylation reaction by introducing the carbon monoxide-containing gas stream to a second reactor at a similar or different set of reaction conditions or the reaction can be performed in a first reactor by introducing the carbon monoxide-containing gas stream to the reactor in the presence of a substrate and carrying out the carbonylation reaction at one set of reaction conditions, followed by carrying out an oxidation reaction by introducing the oxygen-containing gas stream to a second reactor at a similar or different set of reaction conditions.

The product contained in the effluent stream from the reactor or reactors is separated from unreacted substrates. This separation process can be e.g. distillation but may be any separation process which affords a sufficiently good separation for the process to be useful.

Preferably, unreacted substrate is recycled to the oxidatine carbonylation reactions.

The oxidative carbonylation reactions may be carried out in the gas phase in an adiabatic or cooled reactor or in a fluidized bed reactor; they may be carried out in the liquid phase in a trickle bed reactor or in a batch reactor; or they may be carried out in any other reactor that may prove useful for the particular reaction.

The reactions of the present invention can be catalyzed either by heterogeneous catalysts or by homogeneous catalysts or by a combination of these. If the reactions are carried out in the liquid phase, a solvent or co-solvent may be used or the liquid may consist mostly of the reaction product. It is assumed that the reactions of the present invention are carried out at elevated pressure and at elevated temperature.

The solvent for the liquid phase reaction may advantageously be expanded with $CO_2$ so as to contain up to 40% by weight $CO_2$.

Super-critical carbon dioxide can be used as solvent for the oxidative carbonylation reaction.

All of the embodiments of the invention can include the further step of separating the chemical product from the carbon dioxide and recycling the separated carbon dioxide to the electrolysis stage.

The advantages of the invention are as follows:

a) Generation of CO as well as $O_2$ as separate gases of high purity.

b) Omitting syngas production, $CO/H_2$ separation as well as air separation.

c) Avoiding the risks and costs connected with storage, handling and transportation of CO and $O_2$.

d) Consumption of $CO_2$ thus having the potential of reducing the global concentration of greenhouse gases.

e) The option of diluting the reacting gases with $CO_2$ (present in the process in advance) which is very often an advantage in oxidation reactions since it may lead to better temperature control, higher selectivity and some times even to higher reaction rates. This subject is treated e.g. in [Sang-Eon Park and Jin S. Yoo *Studies in Surface Science and Catalysis* 153 (2004) 303-314].

f) The option of using super-critical $CO_2$ as solvent for the oxidative carbonylation reaction since $CO_2$ is already at hand by necessity.

g) The option of using $CO_2$-expanded liquid solvents for the reaction or optionally one of the reactions. The use of $CO_2$-expanded solvents is well known to increase solubility of other gases (e.g. CO and $O_2$) in the liquid reaction medium. $CO_2$ is available in the process in advance.

h) The option of using a reaction product as a solvent for capturing $CO_2$ from a source of dilute $CO_2$. Both DMC and other dialkyl carbonates as well as e.g. 1,3-propanediol are likely to be good solvents for $CO_2$. This embodiment of the invention represents a further integration step.

EXAMPLES

Example 1A

Combined oxidative carbonylation of methanol to dimethyl carbonate (DMC):

$$2CH_3OH+CO+\tfrac{1}{2}O_2=CH_3OCOOCH_3+H_2O \qquad 4)$$

The reaction can be catalyzed by CuCl, alternatively $Cu(OCH_3)Cl$, by Cu-Zeolite Y, by Pd-based or Cu—Pd based catalysts, by Au-based catalysts and possibly other catalysts. It is preferred to use a catalyst which does not demand chlorine (in any form) to be active since chlorine containing compounds may give rise to corrosion problems and undesired contamination of the product. Instead of using methanol as substrate it is possible to use other alcohols, glycols or polyols. Thus, using ethanol will produce diethyl carbonate; using ethylene glycol will produce ethylene carbonate etc. Similarly, ethers may be used as substrate instead of alcohols, whereby carbonate esters would be produced without the co-production of water.

Example 1B

Successive oxidative carbonylation of methanol to dimethyl carbonate using methyl nitrite as intermediate:

$$2CH_3OH+2NO+\tfrac{1}{2}O_2=2CH_3ONO+H_2O \qquad 5)$$

$$2CH_3ONO+CO=CH_3OCOOCH_3+2NO \qquad 6)$$
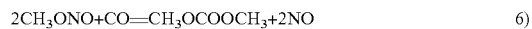

Reaction 5) may be carried out as an uncatalyzed gas phase reaction. Reaction 6) can also be carried out in the gas phase catalyzed e.g. by Pd-containing catalysts such as Pd supported on alumina.

In one embodiment of the invention, methanol is synthesized from CO generated at the cathode by application of the water gas shift reaction to convert part of the CO to $H_2$, followed by traditional methanol synthesis catalyzed e.g. by a Cu/Zn/Al catalyst. Excess $O_2$ generated at the anode can be vented or used for other purposes. For the DMC synthesis either Example 1A or Example 1B or any oxidative carbonylation can be used. In this particular embodiment of the invention the product DMC will be made entirely from $CO_2$.

In another embodiment of the invention the current needed for the $CO_2$ electrolysis is supplied fully or in part in the form of renewable energies such as a photovoltaic device. The electric current may optionally be stored intermediately in a suitable battery device to assure an even production.

Example 2

Oxidation of ethylene to ethylene oxide followed by carbonylation to β-propiolactone (Successive oxidative carbonylation):

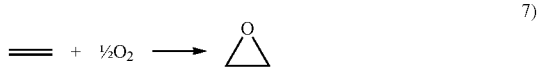

7)

8)

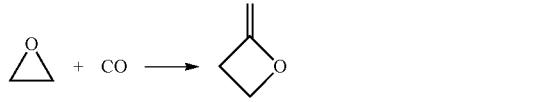

It is possible to choose other olefins than ethylene. Thus, using propylene to generate propylene oxide in reaction 7)

and methyl-propiolactone in reaction 8) is one alternative embodiment of the invention. Other olefins that may be used are 1-butene, 2-butene, styrene, cyclopentene, cyclohexene etc.

Example 3

Carbonylation of propene in the presence of $H_2O$ or an alcohol (ROH, where R may be H or an alkyl group) to give isobutyric acid or an ester of isobutyric acid, followed by oxidation to methacrylic acid or an alkyl methacrylate (Successive oxidative carbonylation):

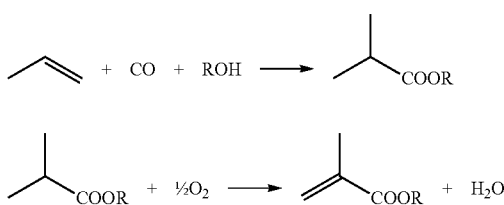

Reaction 9) can be catalyzed by strong acids while reaction 10) can be catalyzed by e.g. a Bi—Fe oxide catalyst.

The above examples 1-3 serve to illustrate the scope of the invention but are not intended to limit the invention. Dimethyl carbonate (DMC) is considered to be a highly versatile compound. It may replace hazardous chemicals such as dimethyl sulphate in methylation reactions and phosgene in carbonylation reactions (e.g. for the production of isocyanates). It is furthermore an excellent and environmentally benign solvent for many chemicals and polymers and has even found use in electrolyte formulations for lithium based batteries. Furthermore, DMC has a high octane number and may be used as a liquid fuel either in a blend with gasoline or (potentially) as the sole component. Some say that it may also be used as a diesel fuel. However, the relatively high production cost of DMC has until now limited its use. β-propiolactone may be used for making a wide range of useful chemicals. Thus, it may be reacted to acrylic acid and polyacrylates, it may be hydrogenated e.g. over a Ni-, Cu- or Pd-based catalyst to yield 1,3-propanediol, it can be hydrolyzed to 3-hydroxy propanoic acid and several more. Methacrylic acid and methacrylate esters are widely used for making polymers.

The invention claimed is:

1. Process for the production of a chemical compound from a carbon dioxide comprising a starting material, comprising the steps of:
   a) providing a feed stream comprising carbon dioxide;
   b) electrolysing in an electrolysis stage at least a part of the amount of the carbon dioxide in the feed stream to a first gas stream containing carbon monoxide and a second gas stream containing oxygen, wherein the molar ratio between carbon monoxide and oxygen is about 1:0.5;
   c) introducing carbon dioxide into the first and/or the second gas stream either by maintaining a degree of conversion of carbon dioxide in the electrolysis stage of less than 100% and/or sweeping either the first or the second gas stream or both gas streams with a sweep gas containing carbon dioxide and/or at some stage between the electrolysis stage and a subsequent reaction stage with a gas containing carbon dioxide to obtain a first process stream containing carbon monoxide and a second process stream containing oxygen, wherein the first and/or second process stream further contains carbon dioxide and the molar ratio of carbon monoxide in the first process stream to oxygen in the second process stream is about 1:0.5; and
   d) introducing the first and second process stream into the reaction stage and reacting the first and second process stream combined or in succession with a substrate to the chemical compound by means of an oxidative carbonylation reaction with the carbon monoxide and oxygen contained in the process feed stream, wherein the substrate is an alcohol or an olefin.

2. The process of claim 1, wherein the substrate is reacted with the first carbon monoxide containing process stream prior to be reacted with the second oxygen containing process stream.

3. The process of claim 1, wherein the substrate is reacted with the second oxygen containing process stream prior to be reacted with the first carbon monoxide containing process stream.

4. The process of claim 1, wherein the electrolysis stage is carried out in a solid oxide electrolysis cell.

5. The process of claim 1, wherein the substrate is methanol.

6. The process of claim 1, wherein the substrate is ethylene.

7. The process of claim 1, wherein the substrate is propene.

8. The process of claim 1, wherein the chemical compound is used as a solvent for capturing carbon dioxide.

9. The process of claim 1, wherein the oxidative carbonylation reaction is carried out in a single reactor in the gas phase.

10. The process of claim 1, wherein the oxidative carbonylation reaction is carried out in a single reactor in the liquid phase.

11. The process of claim 1, wherein the oxidative carbonylation reaction is carried out in two successive reactors in the gas phase or in the liquid phase.

12. The process of claim 1, wherein a solvent for the liquid phase reaction is expanded with $CO_2$ so as to contain up to 40% by weight $CO_2$.

13. The process of claim 1, wherein super-critical carbon dioxide is used as solvent for the oxidative carbonylation reaction.

14. The process of claim 1, wherein unreacted substrate is recycled to the oxidative carbonylation reaction.

15. The process of claim 1, including the further step of separating the chemical product from the carbon dioxide and recycling the separated carbon dioxide to the electrolysis stage.

16. The process of claim 1, wherein the carbon monoxide containing gas stream and the oxygen containing gas stream obtained in step b) are not combined prior to introduction into step d).

17. The process of claim 1, wherein the carbon monoxide containing gas stream from step b) is mixed with the oxygen containing stream from step b) prior to introduction into step d).

18. The process of claim 1, wherein current needed for the electrolysis of carbon dioxide is provided fully or in part by conversion of solar or wind energy.

* * * * *